United States Patent [19]

Malec

[11] 4,065,499

[45] Dec. 27, 1977

[54] LUBRICANT ADDITIVE

[75] Inventor: Robert E. Malec, Birmingham, Mich.

[73] Assignee: Ethyl Corporation, Richmond, Va.

[21] Appl. No.: 613,343

[22] Filed: Sept. 15, 1975

Related U.S. Application Data

[60] Continuation-in-part of Ser. No. 395,221, Sept. 7, 1973, abandoned, which is a division of Ser. No. 255,223, May 19, 1972, Pat. No. 3,778,371, which is a continuation-in-part of Ser. No. 138,758, April 29, 1971, abandoned.

[51] Int. Cl.$^2$ ............................................. C07C 87/00
[52] U.S. Cl. ............................................. 260/567.6 M
[58] Field of Search .................. 260/567.6 M, 567.6 P

[56] References Cited

U.S. PATENT DOCUMENTS

| | | |
|---|---|---|
| 2,129,264 | 9/1938 | Baxter et al. ...................... 260/567.6 |
| 2,592,273 | 4/1952 | Goebel et al. ...................... 260/567.6 |
| 3,033,665 | 5/1962 | Gaston et al. ...................... 260/567.6 |
| 3,079,220 | 2/1963 | Boies et al. ........................ 260/567.6 |
| 3,438,757 | 4/1969 | Honnen et al. ..................... 260/583 R |
| 3,486,866 | 12/1969 | Stromberg et al. ................ 260/667.6 |
| 3,506,712 | 4/1970 | Capowski et al. .................. 260/567.6 |
| 3,778,371 | 12/1973 | Malec ................................. 260/567.6 |

*Primary Examiner*—Bernard Helfin
*Assistant Examiner*—James H. Reamer
*Attorney, Agent, or Firm*—Donald L. Johnson; Robert A. Linn; Joseph D. Odenweller

[57] ABSTRACT

High molecular weight N-hydrocarbyl-substituted quaternary ammonium salts in which the hydrocarbyl group has a molecular weight of from about 350–3000 such as a polybutene ammonium chloride are effective detergents and dispersants for gasoline and lubricating oils.

6 Claims, No Drawings

LUBRICANT ADDITIVE

PRIOR APPLICATIONS

This application is a continuation-in-part of application Ser. No. 395,221, filed Sept. 7, 1973, now abandoned which in turn is a division of application Ser. No. 255,223, filed May 19, 1972, now U.S. Pat. No. 3,778,371, which in turn is a continuation-in-part of application Ser. No. 138,758, filed Apr. 29, 1971, now abandoned.

BACKGROUND

High molecular weight hydrocarbyl amines such as polybutene amines and polyamines are known as detergents and dispersants in fuels and lubricants (Wagenaar, U.S. Pat. No. 3,275,554; Honnen et al, U.S. Pat. No. 3,438,757; Honnen et al, U.S. Pat. No. 3,565,804). These compounds are prepared by reacting an appropriate hydrocarbyl halide with a primary or secondary amine or polyamine under conditions such that hydrogen halide is eliminated.

Low molecular weight quaternary ammonium thiocarbamates and thiophosphates, such as dioleyl dimethylammonium dithiocarbamate or alkylbenzyl dimethyl hydroxyethylammonium O,O-dialkylphosphorodithioate, have been evaluated as antioxidants in lubricating oils (B. W. Hotten, Preprints, ACS Division of Petroleum Chemistry, Vol. 13, No. 2, pages B-67-71, April 1968). Low molecular weight hydrocarbyl ammonium hydroxides, such as dioleyl dimethylammonium hydroxide, a strong base, have been used in gasoline as carburetor detergents (Barusch et al, U.S. Pat. No. 3,468,640).

SUMMARY OF THE INVENTION

The present invention relates to new high molecular weight quaternary ammonium salts having an aliphatic hydrocarbon group with a molecular weight of from about 350–3000 bonded to a quaternary ammonium nitrogen atom. The anion of the salt may be any of the well-known salt anions, such as the halides (chloride, bromide, fluoride, iodide), nitrite, nitrate, carbonate, borate, alkylborates, bicarbonate, alkanoate (e.g., acetate), phosphate, alkylphosphates, dialkylphosphates, dialkyldithiophosphates, and the like. The new compounds are useful as ashless dispersants in lubricating oils and as carburetor detergents in gasoline.

DESCRIPTION OF THE PREFERRED EMBODIMENTS

A preferred embodiment of this invention is a high molecular weight quaternary ammonium salt having at least one aliphatic hydrocarbon group having an average molecular weight of from about 350–3000 bonded to a quaternary ammonium nitrogen atom.

These compounds can be represented by the formula:

$$\begin{bmatrix} R_2 \\ | \\ R_1-N-R_3 \\ | \\ R_4 \end{bmatrix}^+ Z^- \quad (I)$$

in which at least one of $R_1$, $R_2$, $R_3$, and $R_4$ is an aliphatic hydrocarbon group having a molecular weight of about 350–3000 and the remaining R groups are independently selected from $C_{1-20}$ alkyl, $C_{2-8}$ hydroxyalkyl, $C_{3-20}$ alkenyl, or are joined to form a morpholine, piperidine or pyridine ring, and Z is a salt anion. Preferably the high molecular weight hydrocarbon group is substantially saturated, although minor amounts of unsaturation up to about 5 percent are acceptable. It is also preferred that only one of $R_1$, $R_2$, $R_3$ and $R_4$ is a high molecular weight substantially saturated aliphatic hydrocarbon group.

The quaternary ammonium salt may be the quaternary ammonium salt of a polyamine wherein the nitrogen atom in Formula (I) represents but one quaternary ammonium nitrogen atom in said polyamine and is joined through one of the R groups to one or more other quaternary ammonium nitrogen atoms. In this case the bridging group represented by one or more of the R groups is a divalent hydrocarbon group containing from 2 to about 4 carbon atoms, such as an ethylene ($-CH_2-CH_2-$) group. An example is the high molecular weight aliphatic hydrocarbyl quaternary ammonium salt of N,N,N',N'-tetraalkyl ethylene diamine such as N,N,N',N'-tetraethyl ethylene diamine. Likewise, two of the R groups may form a bridge to a single quaternary ammonium nitrogen atom such as would be derived by quaternarizing an N,N'-dialkyl piperazine. In these embodiments one or more of the tertiary nitrogen atoms may be quaternarized.

In an especially preferred embodiment, three of the R groups are ethylene groups and form a bridge to a second nitrogen atom. These compounds are quaternary ammonium salts of the compound triethylenediamine, a cage structure compound having the formula:

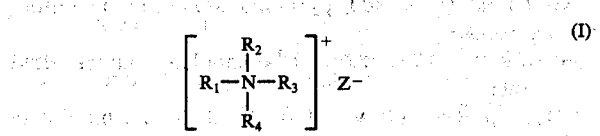

Since this compound has two tertiary nitrogen atoms it is possible to make both mono- and di- high molecular weight aliphatic hydrocarbon quaternary ammonium salts having the following formula:

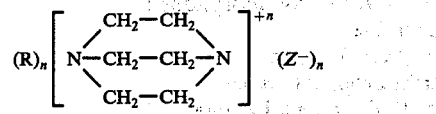

wherein R is a substantially saturated aliphatic hydrocarbon group having an average molecular weight of from 350–3000, more preferably from about 800–1400, and n is 1 or 2. In practice, the salts are generally mixtures of both mono- and di- aliphatic hydrocarbon quaternary ammonium salts such as mono- and di- polybutene quaternary ammonium chlorides, phosphates, alkylphosphates, dialkylphosphates, borates, alkyl borates, nitrites, nitrate, carbonate, bicarbonate, alkanoate, and O,O-dialkyldithiophosphate. The preferred alkyl groups in the foregoing anions are the lower alkyls containing 1 to about 12 carbon atoms, e.g., O,O-diisobutyldithiophosphate. Aryl groups can be substituted for alkyl and are considered equivalent. The alkanoates can contain some unsaturation which can be referred to as alkenoates and, in fact, fatty acid anions, e.g., stearates, oleates, and the like, are very useful. The preferred anions are O,O-dialkyldithiophosphates and chlorides.

The quaternary ammonium salts can be made by known methods such as reacting a high molecular weight aliphatic hydrocarbon halide in which the hydrocarbon group has a molecular weight of from about 350–3000 with an appropriate tertiary amine at 20°–200° C., as depicted in the following equation:

$$R_1-Z + NR_2R_3R_4 \rightarrow I$$

In this reaction, $R_1$ is a high molecular weight (350–3000)aliphatic hydrocarbon, and $R_2$, $R_3$ and $R_4$ are the same as in Formula (I) and Z is a chloride, bromide, iodide, or fluoride anion as represented by Z in Formula (I). Solvents such as aliphatic hydrocarbons boiling from 50°–200° C. can be used as well as aromatic hydrocarbons such as benzene, toluene, xylene, and the like. The reaction results in the formation of a high molecular weight hydrocarbyl-substituted quaternary ammonium halide. The halide anion can be readily replaced by another anion by known methods such as adding a large stoichiometric excess of a salt containing the desired replacement anion to the quaternary ammonium chloride and stirring at 50°–200° C. to displace the chloride anion. The mixture can then be filtered and water washed.

Also, as described above, the tertiary amine used in preparing the quaternary ammonium salt may be a polyamine containing tertiary amine groups. Some representative examples of amine reactants which can be quaternarized to yield compounds of this invention are:
trimethyl amine
triethyl amine
tri-n-propyl amine
dimethylethyl amine
dimethyl lauryl amine
dimethyl oleyl amine
dimethyl stearyl amine
dimethyl eicosyl amine
dimethyl octadecyl amine
N-methyl piperidine
N,N'-dimethyl piperazine
N-methyl-N'-ethyl piperazine
N-methyl morpholine
N-ethyl morpholine
N-hydroxyethyl morpholine
pyridine
triethanol amine
triisopropanol amine
methyl diethanol amine
dimethyl ethanol amine
lauryl diisopropanol amine
stearyl diethanol amine
dioleyl ethanol amine
dimethyl isobutanol amine
methyl diisooctanol amine
dimethyl propenyl amine
dimethyl butenyl amine
dimethyl octenyl amine
ethyl didodecenyl amine
dibutyl eicosenyl amine
triethylene diamine
hexamethylene tetramine
N,N,N', N'-tetramethylethylenediamine
N,N,N', N'-tetraethyl-1,3-propanediamine
methyldicyclohexyl amine
lutidine From the above, it is apparent that the particular amine is not critical. The critical feature of the invention is the long aliphatic hydrocarbon group having an average molecular weight of from about 350–3000, and preferably 800–1400, and having a quaternary ammonium salt group at one end. Any quaternary ammonium salt group will perform, although not all to the same degree of effectiveness, as long as the high molecular weight aliphatic hydrocarbyl group is attached to the quaternary ammonium nitrogen atom. Such high molecular weight aliphatic hydrocarbyl groups contain from about 25 to over 200 carbon atoms.

The aliphatic hydrocarbon group can be any such group that has the required molecular weight. For example, the group may be obtained from mineral oil sources such as the thermal cracking of paraffin wax. The preferred hydrocarbon groups are those derived from polymonoolefins, such as polyethylenes, polypropylenes, polybutenes, polyhexenes, polyoctenes, polydecenes, polydodecenes, and the like. Preferably, the olefin monomers are 1-olefins. The polyolefins made from $C_{2-4}$ olefin monomers are preferred such as polypropylene and polybutene. Of these, polybutene, such as polyisobutylene, is especially preferred because of the good performance of the products obtained and the commercial availability of the polybutenes. The quaternary salts prepared from polyolefin halides such as polybutene chloride are referred to as polyolefin quaternary ammonium salts, e.g., polybutene pyridinium chloride, polybutene tri-lower alkyl ammonium chloride, or mono- or di- polybutene quaternary ammonium chloride of triethylenediamine.

The molecular weight of the aliphatic hydrocarbon group is very important. The lower aliphatic hydrocarbon groups do not impart the all around effectiveness, especially as ashless lubricating oil dispersants, that results when a high molecular weight aliphatic hydrocarbon group is bonded to the quaternary ammonium nitrogen atom. A preferred molecular weight range is from about 350–3000. Superior results are obtained when the hydrocarbon group has a molecular weight of from about 800–1400.

As mentioned earlier, the salt anion can be any of the common salt anions, such as chloride, bromide, fluoride, iodide, nitrite, nitrate, borate, alkylborate, carbonate, bicarbonate, alkanoate (e.g., acetate, propionate, butyrate, and the like), phosphate, alkylphosphate, dialkylphosphate, O,O-dialkyldithiophosphate, and the like. The preferred anions are halides. Of these, bromide and chloride are especially preferred. The most preferred anion is chloride.

Representative examples of quaternary ammonium salts of this invention include:
polybutene (m.w. 3000) trimethylammonium chloride
polybutene (m.w. 1000) triethylammonium iodide
polybutene (m.w. 350) tri-n-propylammonium bromide
polypropylene (m.w. 1500) pyridinium dioctylphosphate
$C_{25}H_{51}$ tri-n-butylammonium nitrite
polybutene (m.w. 900) pyridinium-O,O-di-hexyldithiophosphate
polybutene (m.w. 1000) tri-ethanolammonium ethyl borate
polypropylene (m.w. 800) N-ethanolmorpholinium chloride
polypropylene (m.w. 900) tri-methylammonium O,O-di-eicosyl dithiophosphate
dipolybutene (m.w. 900) triethylenediammonium dichloride dipolypropylene (m.w. 1100) triethylenediammonium dichloride N-polybutene (m.w. 850) triethylenediamine chloride N-polybutene (m.w. 1200) triethylenediamine dioctyl dithiophosphate Further examples will be apparent to any chemist by mere inspection of the previous list of tertiary amines which may be quaternarized by a high molecular weight substantially saturated aliphatic hydrocarbon halide to produce the initial quaternary ammonium halide which may, if desired, be converted to various such salts by exchanging anions by known methods.

The quaternary ammonium dispersants and detergents of this invention are more easily made compared to the methods required to prepare similar prior art additives. For example, the preparation of the prior hydrocarbyl amine detergents requires the reaction of an appropriate hydrocarbyl halide with a primary or secondary amine for long periods of time at elevated temperatures. The conditions must be such that the hydrogen halide is eliminated according to the reaction:

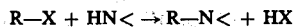

The hydrogen halide formed must be removed or the product could cause corrosion. No such restrictions are placed on the preparation of the present additives. The high molecular weight hydrocarbyl halide is merely mixed with the appropriate tertiary amine and warmed to form the quaternary ammonium salt. Hydrogen halide is not expelled from the reaction.

The high molecular weight aliphatic hydrocarbyl halides used to quaternarize the amine can be made by known methods, such as the well-known halogenation of aliphatic hydrocarbons. The high molecular weight aliphatic hydrocarbon can be obtained from any source, such as the thermal cracking of paraffin wax or, preferably, from the polymerization of olefins. The polyolefin starting material is preferred. The olefins used to prepare the starting material can be any olefin hydrocarbon, such as those containing from 2 to about 32 carbon atoms. The higer olefins such as those containing from 12-32 carbon atoms need not be polymerized to a great extent, but need only be dimerized, trimerized or tetramerized to obtain the required molecular weight. Such olefin polymers are described more fully later, since they can also be used together with compounds of this invention as gasoline additives. Thus, in one embodiment of the invention the polyolefin starting material is a mixture of oligomerized $C_{12-32}$ olefins in which the oligomer has a molecular weight of from about 350-1500.

The preferred polyolefin starting material is the poly-$C_{2-4}$ olefins, especially the poly-$C_{3-4}$ olefins. Any of the polyolefins are readily halogenated by merely passing a halogen into the material at moderate temperatures.

This halogenation can be carried out under relatively mild conditions. The temperature at which the reaction can be carried out may be varied over a wide range. Thus, the halogenation can be accomplished at temperatures ranging from 50° to 150° C. In general, the halogenation is effected by dissolving the polyolefin in a solvent such as benzene, tetrahydrofuran, and the like, and treating the solution with the halogen, for example, chlorine gas, or a halogenating reagent, such as N-bromo succinimide. The polyolefin halide is also obtained by halogenating polyolefin without any solvent being present. The physical characteristics of the polyolefin, for example, its viscosity, will help determine whether a solvent should be used. The halogenation proceeds whether a solvent is used or not. The reaction is generally complete in 15 to 120 minutes. The following examples will illustrate typical halogenation procedures. All parts are by weight unless otherwise specified.

EXAMPLE 1

A solution of 301 parts of Polybutene-24 (Chevron Chemical Company designation for polyisobutylene of molecular weight about 950) in 120 parts of benzene was placed in a vessel equipped with thermometer, stirrer, gas inlet tube and condenser. The solution was heated to about 73° C. and 22.7 parts of chlorine gas was bubbled through over a period of about one hour.

The reaction vessel was then flushed with nitrogen gas for one hour. The solution was filtered and the solvent was removed by vacuum distillation. The yield was 312 parts of polyisobutyl chloride. The product was a cloudy orange-colored viscous liquid, which on analysis was found to contain 3.55 percent chlorine. Infrared analysis showed that the compound was unsaturated.

EXAMPLE 2

A reaction vessel fitted with a thermometer, stirrer and condenser was charged with 94.1 parts of Polybutene-24 (defined in Example 1), 17.8 parts of N-bromo succinimide and 200 parts of benzene. This mixture was refluxed for about 30 minutes. The mixture was then cooled and the solution was filtered. The solvent was stripped and the residue was then redissolved in hexane. This solution was filtered and the solvent was removed by vacuum distillation. A 99 percent yield of the polyisobutyl bromide was obtained as a dark brown viscous liquid. The bromine content of this product was 7.9 percent.

The following example illustrates the halogenation of a polyolefin followed by quaternarization of the resultant hydrocarbyl halide.

EXAMPLE 3

In a reaction vessel was placed 180 parts of polybutene (average molecular weight 800) and 100 parts of benzene. Chlorine was passed into the solution at 80°-90° C. for one hour. The system was then purged of chlorine by passing nitrogen through it for an hour. Following this, 40 parts of pyridine was added and the mixture stirred at 120°-130° C. for 3 hours. The resultant product was washed with water and then heated under vacuum to remove solvent. It was diluted with an SAE-10 neutral mineral oil to form a 50 weight percent active concentrate of polybutene pyridinium chloride in which the polybutene group bonded to the quaternarized pyridinium nitrogen atom had an average molecular weight of 800. Polybutene and polybutenyl as well as polypropylene and polypropenyl when referring to aliphatic hydrocarbon groups are used interchangeably herein.

The following examples illustrate the replacement of the chloride anion with various other anions.

EXAMPLE 4

In a reaction vessel was placed 25 parts of the polybutene pyridinium chloride from Example 3 and 13 parts of O,O-di-$C_{20-30}$ alkyl zinc phosphorodithioate. To this mixture was added about 25 parts of petroleum ether and the mixture was stirred at reflux for 30 minutes. The mixture was cooled and filtered to remove the zinc chloride precipitate and the filtrate washed with water. It was then heated under vacuum to distill out the petroleum ether. The product was an oil-diluted concentrate containing polybutene pyridinium O,O-di-$C_{20-30}$ alkyl phosphorodithioate.

EXAMPLE 5

In a reaction vessel was placed 25 parts of the polybutene pyridinium chloride from Example 3, 25 parts of petroleum ether and 5 parts of sodium nitrite dissolved in a water-methanol mixture. The mixture was heated and stirred for 30 minutes. The small aqueous phase present was then removed and the product heated under vacuum to distill out solvent. The remaining product was filtered, yielding a mixture containing polybutene pyridinium nitrite.

EXAMPLE 6

In a reaction vessel was placed 25 parts of the polybutene pyridinium chloride from Example 3 and 6.25 parts of sodium dibutyl dithiocarbamate. Twenty parts of petroleum ether were added and the mixture stirred at reflux for 30 minutes. The product was filtered and the solvent distilled off under vacuum, resulting in a concentrate contaning polybutene pyridinium dibutyl dithiocarbamate.

EXAMPLE 7

In a vessel was placed 25 parts of the polybutene pyridinium chloride from Example 3 and 5 parts of didecyl hydrogen phosphate. The mixture was stirred and heated under vacuum for one hour, during which period hydrogen chloride evolved. The resultant mixture was an oil concentrate containing polybutene pyridinium tridecylphosphate.

EXAMPLE 8

In a closed reaction vessel place 1000 parts of polypropylene bromide (made by brominating polypropylene having an average molecular weight of 950). Add 500 parts of toluene and 90 parts of trimethyl amine. Stir and heat the mixture to reflux. Reflux for an hour and then cool and wash twice with 500 part portions of water. Heat to about 150° C. under vacuum (approximately 10 mm Hg) to distill out the toluene solvent. The product is a polypropenyl trimethyl ammonium bromide in which the polypropenyl group has an average molecular weight of 950.

Other amines can be used in the above example with good results. The following table lists such other amines and the corresponding product which forms.

| AMINE | QUATERNARY AMMONIUM SALT |
|---|---|
| triethyl amine | polypropenyl triethyl ammonium bromide |
| lauryl dimethyl amine | polypropenyl lauryl dimethyl ammonium bromide |
| eicosyl dimethyl amine | polypropenyl eicosyl dimethyl ammonium bromide |
| dioleyl methyl amine | polypropenyl dioleyl methyl ammonium bromide |
| distearyl ethyl amine | polypropenyl distearyl ethyl ammonium bromide |
| dilauryl methyl amine | polypropenyl dilauryl methyl ammonium bromide |
| N-methyl piperidine | polypropenyl methyl pyridinium bromide |
| N-methyl morpholine | polypropenyl methyl morpholinium bromide |
| triethanol amine | polypropenyl tri(2-hydroxyethyl)ammonium bromide |
| diethanol ethyl amine | polypropenyl di(2-hydroxyethyl) ethyl ammonium bromide |
| N,N,N',N'-tetramethyl ethylene diamine | polypropenyl tetramethyl ethylene diammonium bromide |
| nitrilotriacetonitrile | polypropenyl triaceto nitrile ammonium bromide |

EXAMPLE 9

In this example the starting hydrocarbon is an olefin oligomer prepared by polymerizing a mixture of $C_{12-32}$ 1-olefins using an aluminum chloride catalyst to obtain an oligomer having an average molecular weight of 550. The preparation of this oligomer will be described later.

In a reaction vessel place 550 parts of the above oligomer and heat to 80°–90° C. Pass chlorine into the liquid until one mole part has reacted. Following this, pass nitrogen through the liquid for 10 minutes to remove residual chlorine. Then add 100 parts of pyridine and 250 parts or toluene. Heat the mixture to 130° C. and stir for an hour. Cool and wash with water and then distill out the toluene under vacuum. Add 630 parts of an SAE-10 neutral mineral oil to obtain a 50 weight percent active concentrate of a poly-$C_{12-32}$ 1-olefin pyridinium chloride.

Other hydrocarbons having an average molecular weight of from about 350–3000 can be used in the above example in place of the poly-$C_{12-32}$ 1-olefin. These can be obtained directly from mineral oil or can be thermally cracked paraffin wax. Likewise, polymers of lower 1-olefins such as polypropylene or polyisobutylene can be used with excellent results.

EXAMPLE 10

In a reaction vessel was placed 200 grams of polybutene chloride (from polybutene having an average molecular weight of 950) and 30 grams of dimethyl acetamide. The mixture was heated to 90° C. and trimethylamine was bubbled through it for 1.75 hours. The resultant product was distilled under vacuum to remove volatiles and the residual liquid diluted with 100 grams of light mineral oil, giving a detergent concentrate of polybutene trimethyl ammonium chloride.

EXAMPLE 11

In a reaction vessel was placed 20 grams of the polybutene trimethylammonium chloride from Example 10 and 2 grams of hexyleneglycol acid borate. The mixture was stirred and heated on a stem bath for one hour and then distilled under vacuum, yielding a polybutene trimethylammonium hexyleneglycol borate.

EXAMPLE 12

In a reaction vessel as used in Example 1 was placed 200 grams of polybutene chloride prepared as in Example 1. To this was added 13.4 grams of triethylenediamine and 40 grams of methylethyl ketone solvent. The mixute was stirred at 130°–137° C. for one hour and then diluted with 75 grams of light mineral oil and 30 grams of n-dodecanol. The concentrate was diluted with an equal volume of hexane and washed first with lime water and then with water. It was the filtered and the volatiles distilled out under vacuum, yielding 303 parts of a dispersant concentrate (approximately 67 percent active).

EXAMPLE 13

In a reaction vessel as used in Example 1 was placed 50 grams of polybutene chloride (from Example 1), 7 parts of hexamethylenetetramine and 15 parts of N,N-dimethyl acetamide solvent. The mixture was stirred for 75 minutes at 150°-155° C. to form a polybutenyl quaternary ammonium chloride of hexamethylenetetramine.

EXAMPLE 14

In a reaction vessel was placed 100 grams of polybutene chloride (from Example 1) and 200 grams of pyridine. The mixture was stirred at 188° C. for 3.5 hours, following which unreacted pyridine was distilled out at reduced pressure. The product was diluted with an equal volume of hexane and filtered. The hexane was distilled out and the product diluted with 54 grams of light mineral oil to give 163 grams of 67 percent active polybutenyl pyridinium chloride.

The alkyl hydrogen phosphate salt was prepared by heating a mixture of n-decanol and dodecanol and $P_2O_5$ for 2 hours at 90°-95° C. It was diluted with petroleum ether and water washed. It was converted to its sodium salt by adding 53 grams of sodium hydroxide to bring the pH to 8-9.

The above polybutenyl pyridinium chloride was converted to an alkyl phosphate salt by mixing 50 grams of the chloride salt with 5 grams of the above sodium alkyl phosphate, diluting the mixture with hexane and stirring for ½ hours at reflux. The product was washed with water to remove sodium chloride and the hexane distilled out under vacuum to leave a polybutenyl pyridinium alkyl phosphate.

EXAMPLE 15

In a reaction vessel was placed 634 grams of polybutene chloride (average molecular weight 950) and 500 ml of chlorobenzene. The mixture was heated to 130° C. and chlorine injected for one hour and 35 minutes. Solvent was distilled out, leaving a polybutene chloride.

In a second reaction vessel was placed 100 grams of the above polybutene chloride, 6.7 grams of triethylenediamine and 50 grams of methylethyl ketone. The mixture was stired one hour at 90°-93° C., diluted with hexane, water washed and filtered. It was then diluted with 50 grams of light mineral oil and distilled under vacuum to remove volatile materials.

EXAMPLE 16

One-half of the product prepared in Example 15 was added to a saturated solution of sodium nitrite in dimethylformamide. The mixture was heated to reflux and stirred 30 minutes following which it was washed with water and distilled to remove volatiles, resulting in a residue containing polybutenyl quaternary ammonium nitrite salt of triethylenediamine.

The quaternary ammonium salts of this invention are excellent dispersants for lubricating oil including both synthetic (e.g., ester based oils) and mineral lubricating oils. Tests were carried out to demonstrate their effectiveness.

SLUDGE DISPERSANCY TEST

In this test a test blend is prepared using 7 grams of a typical engine sludge material, 2 grams of water, one gram of test additive and sufficient neutral mineral oil to make a 100 gram blend. This material is emulsified in a blender for 20 minutes and then centrifuged for 2.5 hours. Following this, the percent light transmittance of the oil just beneath the surface is measured photoelectrically. The better the dispersant, the move of the sludge that will remain suspended following the centrifuging, and hence the lower the percent light transmittance that will be measured. The light transmittance of the test oil is compared to the transmittance of the base oil subject to the same conditions but without any dispersant. This shows the degree of dispersant effectiveness. The following results were obtained.

| Additive of | Conc. (Wt. %) | Percent Light Transmittance |
| --- | --- | --- |
| None | — | 59 |
| Example 3 | 1 | 1 |
| Example 4 | 1 | 2 |
| Example 5 | 1 | 11 |
| Example 6 | 1 | 26 |
| Example 7 | 1 | 1 |
| Example 13 | 0.5 | 4 |
| Example 13 | 1.0 | 1 |
| Example 12 | 0.5 | 3,4,7,9,14 |

As the above tests show, the dispersants of the present invention retained the sludge in a dispersed form even after 2.5 hours of centrifuging to such a degree that as little as 1 percent of the light would transmit through the oil compared to 59 percent of the light which was transmitted through the non-dispersant oil.

Additives of this invention have been subjected to engine tests. The test employed were standard L-43 single cylinder tests in which an engine is operated under controlled conditions and the amount of sludge and varnish accumulated on various engine components is visually rated periodically on a scale from 0-10 (10 being perfectly clean). The test criteria is the number of hours until the average sludge and varnish rating drops to 9. The test oil contained 0.08 percent zinc as a commercial zinc dialkyldithiophosphate. The results obtained were as follows:

| Additive | Conc. % | Hours Sludge | Varnish |
| --- | --- | --- | --- |
| none | — | 39 | 48 |
| Example 14 | 0.5 | 43 | 60+ |
| Example 12 | 0.5 | 52 | 60+ |
| commercial disp.* | 0.5 | 55 | 60+ |

*A commercial high molecular weight alkenyl succinimide of polyethylenepolyamine, e.g., tetraethylenepentamine.

The additives of this invention are useful dispersants in both mineral and synthetic lubricating oils. Examples of mineral lubricating oils include those refined from any crude oil such as Pennsylvania, midcontinent, Gulfcoast, California and the like. The synthetic lubricants include both the hydrocarbon type and the other various types of synthetic lubricants. Hydrocarbon synthetic lubricants are generally polyolefin oligomers or alkylated aromatics. Examples are polybutene oligomers, styrene isobutylene copolymers, γ-decene trimers, tetramers, pentamers, and mixtures thereof, mixtures of alkylated benzenes from $C_{12-26}$ olefins and having an average molecular weight of 450, and the like. The polyolefin oligomers are readily prepared from the appropriate olefin by standard oligomerization catalysts such as aluminum chloride, boron trifluoride, diethyl aluminum chloride, ethyl aluminum sesquichloride, combinations of aluminum alkyls and metal salts such as diethyl aluminum chloride-titanium tetrachloride, ethyl aluminum sesquichloride-butyl vanadates, triethyl aluminumzirconium iodides, and the like.

The alkylated aromatics are made by alkylating aromatics such as benzene, toluene, naphthalenes, and the like, with olefin mixtures preferably containing $C_{12-32}$ olefins. Catalysts such as $AlCl_3$ and $BF_3$ are effective and the average molecular weight of the product should be from about 300 to 600.

The additives are very effective in synthetic ester type lubricants including monoesters, diesters, complex esters, and the like. Some examples are $C_{5-10}$ aliphatic monocarboxylic acid esters of trimethylolpropane, n-hexanioc ester of pentaerythritol, $C_{5-9}$ aliphatic monocarboxylic esters of equal mole mixtures of trimethylolpropane and pentaerythritol, adipic acid diesters of $C_{7-12}$ monohydric alkanols, complex esters formed by esterifying mixtures of polyols, dicarboxylic acids and monocarboxylic acids. For example, a useful complex ester is formed by condensing adipic acid, ethyleneglycol and a $C_{5-10}$ mixture of aliphatic monocarboxylic acids. Another complex ester is formed from trimethylolpropane, adipic acid and $C_{10-12}$ fatty alcohol mixtures. In essence, the complex esters are condensation products of polycarboxylic acids, polyols, and either monocarboxylic acids or monohydric alkanols, or both.

Other synthetic lubricants include the polyalkyl siloxanes, polyalkyl silicates, alkyl silicones, polyfluoro hydrocarbons, polyaryl ethers, polyalkoxy aryls, polyglycols, and the like.

The lubricant compositions are prepared by merely blending a dispersant amount of the additive with the oil. An effective amount is usually from about 0.1 to 5 weight percent, although more or less can be beneficially employed.

The lubricant compositions can include the other ingredients normally added to formulated lubricants. For example, mineral oil and synthetic hydrocarbon oil lubricants generally include zinc dialkyldithiophosphates, calcium alkyl sulfonates, overbased calcium sulfonates containing colloidal calcium carbonate, calcium phenates, antioxidants such as 4,4'-methylenebis-(2,6-di-tert-butylphenol), 2,6-di-tert-butyl-α-dimethyl amino-p-cresol, phenylene diamines, barium phosphonates, polyalkyl methacrylate V.I. improvers, and the like. Synthetic ester formulations may include phosphate ester wear inhibitors such as tricresyl phosphate, phenyl dicresyl phosphate, and the like, antioxidants such as phenyl-β-naphthyl amine, phenylene diamines, phenothiazines, and the like, metal deactivators, silicone antifoam agents, and the like.

The following examples illustrate the preparation of some preferred lubricant compositions of this invention.

EXAMPLE 17

In a blending vessel is placed 10,000 parts of solvent-refined, midcontinent, neutral mineral oil (100 SUS). To this is added 100 parts of zinc diisobutyl dithiophosphate, 150 parts of overbased calcium alkaryl sulfonate (300 base number), 200 parts of polylaurylmethacrylate V.I. improver, and 50 parts of 4,4'-methylenebis-(2,6-di-tert-butylphenol). Following this, 35 parts of polyisobutene pyridinium chloride of Example 3 is added. The mixture is warmed to 50° C. and stirred until homogenous, giving a lubricant of good stability and excellent dispersant properties suitable for use in automotive engines.

EXAMPLE 18

In a blending vessel is placed 10,000 parts of a hindered ester lubricant made of esterifying trimethylolpropane with a mixture of $C_6$ and $C_8$ n-aliphatic carboxylic acids. Following this, there is added 100 parts of phenyl-α-naphthyl amine, 100 parts of dioctyldiphenyl amine, 10 parts of 1-salicylalaminoguanadine, 300 parts of tricresyl phosphate, and .05 part of dimethyl silicone. Then, 300 parts of the polypropenyl trimethyl ammonium bromide of Example 8 is added. The mixture is warmed to 50° C. and stirred for 15 minutes. It is then filtered to give a synthetic ester lubricant suitable for use in turbines and turbojet engines.

The manner in which the additive is blended with the other lubricants mentioned is apparent from the foregoing examples.

The additives of this invention are also useful as detergents in liquid hydrocarbon fuels including distillate fuels, such as diesel fuel and liquid hydrocarbon fuels of the gasoline boiling range. Liquid hydrocarbon fuels of the gasoline boiling range are mixtures of hydrocarbons having a boiling range of from about 80° F. to about 430° F. (ASTM D-86). Of course, these mixtures can contain individual constituents boiling above or below these figures. These hydrocarbon mixtures contain aromatic hydrocarbons, saturated hydrocarbons and olefinic hydrocarbons. The bulk of the hydrocarbon mixture is obtained by refining crude petroleum by either straight distillation or through the use of one of the many known refining processes, such as thermal cracking, catalytic cracking, catalytic hydroforming, catalytic reforming, and the like. Generally, the final gasoline is a blend of stocks obtained from several refinery processes. The final blend may also contain hydrocarbons made by other procedures such as alkylate made by the reaction of $C_4$ olefins and butanes using an acid catalyst, such as sulfuric acid or hydrofluoric acid.

Preferred gasolines are those having a Research Octane Number of at least 85. A more preferred Research Octane Number is 90 or greater. It is also preferred to blend the gasoline such that it has a content of aromatic hydrocarbons ranging from 10 to about 60 volume percent, an olefinic hydrocarbon content ranging from 0 to about 30 volume percent, and a saturate hydrocarbon content ranging from about 40 to 80 volume percent, based on the whole gasoline.

The amount of the detergent added to the fuel should be at least sufficient to exert some detergent action in the fuel induction system. In other words, it should be a detergent amount. Detergent action is generally attained when the fuel contains from about 10-2000 ppm (parts per million) of the new detergent, and more preferably, when it contains from about 20-1000 ppm.

The gasoline may contain any of the other additives normally employed to give fuels of improved quality, such as tetraalkyllead antiknocks including tetramethyllead, tetraethyllead, mixed tetraethyltetramethyl lead, and the like. They may also contain antiknock quantities of other agents such as cyclopentadienyl nickel nitrosyl, methylcyclopentadienyl manganese tricarbonyl and N-methyl aniline, and the like. Antiknock promoters such as tert-butyl acetate may be included. Halohydrocarbon scavengers such as ethylene dichloride, ethylene dibromide and dibromo butane may be added. Phophorus-containing additives such as tricresyl phosphate, methyl diphenyl phosphate, diphenyl methyl phosphate, trimethyl phosphate, and tris(β- chloropropyl)- phosphate may be present. Antioxidants such as 2,6-di-tert-butylphenol, 2,6-di-tert-butyl-p-cresol, phenylenediamines such as N-isopropylphenylenediamine, and the like, may be present. Likewise, the gasoline can contain dyes, metal deactivators, or any of the additives recognized to serve some useful purpose in improving the gasoline quality.

A preferred embodiment of the invention is a liquid hydrocarbon fuel of the gasoline boiling range containing a detergent amount of the new detergent of this invention and from about 0.25 to 4 grams per gallon of lead as tetraethyllead or tetramethyllead. A still further embodiment of the invention is a liquid hydrocarbon fuel of the gasoline boiling range containing a detergent amount of the new detergent of this invention and from about 0.005 to 3, more preferably 0.005 to 0.5, grams of manganese per gallon as methylcyclopentadienyl manganese tricarbonyl.

A highly preferred embodiment of this invention is a liquid hydrocarbon fuel of the gasoline boiling range as previously described containing in addition to the detergent additive a small amount of a mineral oil. This embodiment is particularly advantageous in promoting the cleaning of intake valves and stems in spark ignited internal combustion engines. The amount of oil added can be any amount from about 0.05 to about 0.5 volume percent, based on the final gasoline. Although the oil adjuvant can be any of the well-known mineral oils, including those obtained from Pennsylvania, midcontinent, Gulfcoast, or California crudes, the more preferred are the naphthenic mineral oils. The viscosity of the mineral oil can vary from about 100 to 2000 SUS at 100° F.

In another preferred embodiment a synthetic olefin oligomer is used in place of or together with the mineral oil adjuvant. These oligomers are prepared by the polymerization of one or more aliphatic monoolefinic hydrocarbons containing from 2 up to about 32 carbon atoms, such as ethylene, propylene, butene, decene-1, eicosene-1, triacontene-1, and the like. These result in such adjuvants as polyethylene, polypropylene, ethylene-propylene copolymer, polybutene, styrene-butadiene copolymer, α-decene trimer, α-decene tetramer and mixtures of the proper average molecular weight.

The gasoline detergent additives of this invention can be added directly to gasoline or they can be added in the form of a concentrate. Thus, another embodiment of the invention is a gasoline detergent concentrate containing an additive amount of a detergent of this invention and a diluent. The amount of detergent in the concentrate can vary from about 10-90 weight percent. A preferred concentration is from about 35-75 weight percent. The diluent serves to maintain the concentrate in a liquid form, making it easy to handle and to meter into gasoline blending systems. Preferred diluents are hydrocarbons including both aliphatic and aromatic hydrocarbons such as hexane, heptane, octane, petroleum ether, kerosene, benzene, toluene, xylene, and the like, including mixtures thereof. A more preferred diluent is a higher boiling hydrocarbon such as a mineral oil or polyolefin oligomer. The advantage of using these higher boiling hydrocarbon diluents is that these higher boiling hydrocarbons also serve as the previously-described mineral oil or polyolefin adjuvants. Thus, a preferred concentrate contains from about 10-90 weight percent, preferably 35-75 weight percent, of the detergent in a mineral oil or polyolefin oligomer. When this concentrate is added to gasoline a fuel is provided which will maintain the entire induction system in a high degree of cleanliness.

Especially good results have been obtained when the hydrocarbon diluent employed in the concentrate is one of the previously-described polyolefin oligomers made by polymerizing an olefin or mixture of olefinic hydrocarbons containing about 12 or more carbon atoms, preferably from 12-32 carbon atoms, to produce a liquid olefin polymer having an average molecular weight of about 300-1500.

The detergent concentrate can contain other additives normally used with gasoline, forming an additive "package". For example, the concentrate can contain gasoline antioxidants such as 2,6-di-tert-butylphenol, mixtures of butylated phenol containing about 75 percent of 2,6-di-tert-butylphenol, 15 percent o-tert-butylphenol, N-isopropylphenylenediamine; phorphorus additives such as tricresyl phosphate, trimethylphosphate, phenyldimethylphosphate, dimethylphenylphosphate, tris($\beta$-chloropropyl)phosphate, and the like; antiknock promoters such as tert-butyl acetate; de-icers such as methanol, isopropanol, n-butanol, isobutanol; tetraalkyllead antiknocks such as tetraethyllead, tetramethyllead, redistributed tetraethyltetramethyllead, and the like; scavengers such as ethylene dichloride, ethylene dibromide, dibromobutanes, and the like; other antiknock agents such as methyl cyclopentadienyl manganese tricarbonyl, ferrocene, methyl ferrocene, cyclopentadienyl nickel nitrosyl, N-methylaniline, and the like; metal deactivators such as N,N'-disalicylidene-1,2-diaminopropane, dyes; corrosion inhibitors, and the like.

The concentrates of this invention are readily prepared by merely blending the ingredients until a homogenous solution is obtained. The following examples illustrate the preparation of some typical concentrates.

EXAMPLE 19

To a blending vessel is added 1000 parts of the detergent product from Example 3 and 1000 parts of a naphthenic mineral oil. The mixture is warmed and stirred until homogenous, forming an additive concentrate useful for improving the detergent properties of gasoline.

EXAMPLE 20

To a blending vessel is added 1000 parts of the detergent additive from Example 5 and 1500 parts of the olefin oligomer. Then, 20 parts of a mixture of butylated phenols containing about 75 percent 2,6-di-tert-butylphenol are added. This mixture is stirred, forming a detergent package which also imparts antioxidant protection when added to gasoline.

The amounts of each ingredient in the foregoing compositions can be varied within wide limits to provide the optimum degree of each property.

Gasoline compositions of this invention can be prepared by merely adding the detergent in the proper amount to the gasoline base stock and stirring until dissolved. Likewise, the detergent can be injected into the gasoline stream in an in-line blending system either alone or in combination with other additives such as tetraalkyllead antiknocks. Similarly, the additive concentrate can be added to gasoline, furnishing not only the detergent but also the adjuvant (mineral oil or olefin oligomer). If desired, the detergent and adjuvant can be separately added to the base gasoline.

The following examples serve to illustrate the manner in which gasoline compositions of this invention are made. In these examples the gasoline base stocks have the following composition and properties.

| Fuel | RON | Boiling Range (°F.) | | Composition | | |
|---|---|---|---|---|---|---|
| | | Initial | End Point | % Aromatics | % Olefins | % Saturates |
| H | 91 | 91 | 390 | 40 | 1.5 | 58.5 |
| I | 86 | 100 | 400 | 35 | 2 | 63 |
| J | 87 | 95 | 410 | 36.5 | 2.5 | 61 |
| K | 95 | 89 | 395 | 49.5 | 2.5 | 48 |
| L | 97 | 105 | 415 | 54 | 1.5 | 44.5 |
| M | 90 | 96 | 389 | 39 | 3 | 58 |
| N | 94 | 87 | 395 | 51 | 0.5 | 48.5 |

EXAMPLE 21

In a blending vessel is placed 10,000 gallons of Gasoline H, 25 pounds of the detergent of Example 3, 100 pounds of the polyisobutylene (mol. wt. 1000), 96.5 pounds of tetraethyllead as a commercial antiknock fluid containing one theory of ethylene dichloride and 0.5 theory of ethylene dibromide, and 15.5 pounds of tricresylphosphate. The mixture is stirred until thoroughly mixed. The resultant gasoline is a premium grade gasoline with good detergent properties.

EXAMPLE 22

In a blending vessel is placed 10,000 gallons of Gasoline L, 2.5 pounds of detergent of Example 5, and 50 pounds of a neutral mineral oil (viscosity 100 SUS at 100° F.). The mixture is stirred, resulting in an unleaded gasoline having good detergent properties.

EXAMPLES 23 – 32

The above Examples 21 and 22 are repeated using each of Gasolines I, J, K, M and N.

EXAMPLE 33

To a blending vessel is added 10,000 gallons of Gasoline I, 100 pounds of the additive package of Example 20, 84 pounds of tetraethyllead as a commercial antiknock fluid, and 4.8 pounds of trimethylphosphate. The mixture is stirred, giving a high quality gasoline of good detergent properties.

Tests were carried out to demonstrate the carburetor detergent properties of the present additive. In these, the additive was added to gasoline which was used to operate a six cylinder L-head engine for 2 hours using exhaust recycle to the carburetor. The carburetor is clean at the start of the test and the criteria of effectiveness is the carburetor deposit weight formed. The results obtained were as follows:

| Additive | Conc. | Carburetor Deposit Wt. (mg) |
|---|---|---|
| none | — | 3.2* |
| Example 10 | 20 ppm** | 1.5, 1.8 |
| Example 11 | 20 ppm | 1.4, 1.5 |
| Example 14 | 20 ppm | 1.3 |

*Average value
**Parts per million

As the test results show, the additives of this invention reduce carburetor deposits to about one-half that normally obtained.

I claim:

1. A high molecular weight quaternary ammonium chloride having at least one substantially saturated poly-$C_{2-4}$ olefin hydrocarbon group having an average molecular weight of from about 800 to about 1400 bonded to a quaternary ammonium nitrogen atom, the remaining groups bonded to said quaternary ammonium nitrogen atom being selected from the group consisting of $C_{1-20}$ alkyl, $C_{2-8}$ hydroxyalkyl and $C_{3-20}$ alkenyl.

2. A quaternary ammonium chloride of claim 1 wherein said poly-$C_{2-4}$ olefin group is a polyethylene group.

3. A quaternary ammonium chloride of claim 1 wherein said poly-$C_{2-4}$ olefin group is a polypropylene group.

4. A quaternary ammonium chloride of claim 1 wherein said poly-$C_{2-4}$ olefin group is a polybutene group.

5. A composition of claim 4 wherein said quaternary ammonium chloride is polybutene tri-$C_{1-4}$ alkyl ammonium chloride.

6. A composition of claim 5 wherein said polybutene tri-$C_{1-4}$ alkyl ammonium chloride is polybutene trimethyl ammonium chloride.

* * * * *